(12) United States Patent
Naotsuka et al.

(10) Patent No.: US 6,387,687 B1
(45) Date of Patent: May 14, 2002

(54) PROCESS FOR PRODUCING INDOLMYCIN

(75) Inventors: Akihiko Naotsuka, Nishinomiya; Motoo Izawa, Amagasaki; Ken-ichiro Miyagawa, Osaka, all of (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/744,340

(22) PCT Filed: Jul. 29, 1999

(86) PCT No.: PCT/JP99/04073

§ 371 Date: Jan. 23, 2001

§ 102(e) Date: Jan. 23, 2001

(87) PCT Pub. No.: WO00/06697

PCT Pub. Date: Feb. 10, 2000

(30) Foreign Application Priority Data

Jul. 30, 1998 (JP) ............................. 10-215650

(51) Int. Cl.[7] .................................. C02N 1/20
(52) U.S. Cl. .................... 435/253.5; 435/108; 435/121; 435/244; 514/292
(58) Field of Search ................. 435/108, 121, 435/244, 253.58; 514/292

(56) References Cited

U.S. PATENT DOCUMENTS 4,560,652 A * 12/1985 Kurahashi et al. .......... 435/108

FOREIGN PATENT DOCUMENTS

JP 62-99306 5/1987

OTHER PUBLICATIONS

Sigma (Biochemicals, Organic Compounds for Research and Diagnostic Agents, 1994, p. 448.*

Difco Manual Difco Laboratories, 1985, Detroit, MI 48232, p. 1136.*

Demain et al., 1986. Manual of Industrial Microbiology and Biotechnology, American Society for Microbiology, Washington, D.C., pp. 442–445.*

R. Werner et al., "Directed biosynthesis of new indolmycins", Journal of Antibiotics. vol. 34, No. 5, pp. 551–554 (1981).

* cited by examiner

*Primary Examiner*—Francisco Prats
*Assistant Examiner*—Kailash C. Srivastava
(74) *Attorney, Agent, or Firm*—Mark Chao; Elaine M. Ramesh

(57) ABSTRACT

A microorganism having indolmycin-producing ability and tryptophan analogue resistance is provided, and indolmycin or its salt can be produced efficiently by cultivating such microorganism in a medium to produce and accumulate indolmycin or its salt in the culture broth followed by recovering a product.

4 Claims, No Drawings

PROCESS FOR PRODUCING INDOLMYCIN

This application is the National Stage of International Application No. PCT/JP99/04073, filed on Jul. 29, 1999.

TECHNICAL FIELD

The present invention relates to a method for producing an antibacterial agent, especially, indolmycin useful as an anti-H.pylori (Helicobacter pylori), by a fermentation.

BACKGROUND ART

Indolmycin is a compound represented by the following formula and useful as a pharmaceutical (for example, an antibacterial agent, especially anti-H.pylori agent), a veterinary agent and a herbicide.

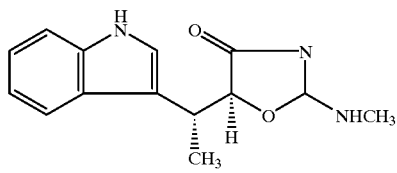

A known method for producing indolmycin by a chemical synthesis is a method described in Journal of Organic Chemistry, Vol.51, p. 4920 (1986). However, this synthesis gives only a racemate since indolmycin contains 2 asymmetric carbon atoms. While another method is described in Chemistry Letters, p.163 (1980), it involves a complicated process for obtaining an optically active indolmycin and has a low yield.

Still another known method for producing indolmycin is a fermentation using Streptomyces griseus ATCC 12648 as a producer microorganism (The Journal of Antibiotics, Vol.27, p.49 (1974), The Journal of Antibiotics, Vol.34, p.551 (1981)), but its low yield is also problematic from an industrial point of view.

Since a conventional method for producing indolmycin cannot satisfactorily be applied to industrial production, a large scale and convenient method for producing indolmycin is desired.

DISCLOSURE OF INVENTION

We made an effort under the circumstance described above to establish a method for producing indolmycin by fermentation, and finally discovered that by obtaining a tryptophan analogue-resistant mutant of Streptomyces griseus and by using it, an accumulation of a large amount of indolmycin in a culture broth can be obtained. We also discovered that by supplementing the medium with L-tryptophan a further higher accumulation can be achieved. We also established a method for obtaining indolmycin conveniently from the culture broth at a higher yield by means of chromatography using an adsorption resin, and a weakly-basic anion exchange resin, a weakly acidic cation exchange resin as a support together with an aqueous organic solvent.

Thus, the present invention relates to:

(1) A microorganism having indolmycin-producing ability and tryptophan analogue resistance;
(2) A microorganism according to the above (1) wherein said microorganism is a microorganism belonging to the Genus Streptomyces;
(3) A microorganism according to the above (1) wherein said microorganism is a microorganism belonging to the species Streptomyces griseus;
(4) A microorganism according to the above (1) wherein said tryptophan analogue is fluoro-DL-tryptophan;
(5) A method for producing indolmycin or its salt comprising cultivating a microorganism according to the above (1) in a medium to allow indolmycin or its salt to be accumulated in the culture broth, and then recovering a product;
(6) A method according to the above (5) wherein L-tryptophan is added to the medium;
(7) A method according to the above (5) wherein 0.2 to 5 g of L-tryptophan is added per 1 L of the medium;
(8) A method according to the above (5) wherein 0.2 to 10 g of anthranilic acid is added per 1 L of the medium;
(9) A method according to the above (5) wherein 0.2 to 3 g of L-tryptophan and 0.2 to 2 g of anthranilic acid are added per 1 L of the medium;
(10) A method according to the above (5) wherein a purification is performed using an adsorption resin, a basic anion exchange resin and/or an acidic cation exchange resin as a support and an aqueous organic solvent as an eluent.

A tryptophan analogue employed in the invention may for example be a halogenated tryptophan such as 5-fluoro-DL-tryptophan (hereinafter sometimes referred to as 5-FT), 6-fluoro-DL-tryptophan (hereinafter sometimes referred to as 6-FT) and the like. One preferable example is 5-fluoro-DL-tryptophan or 6-fluoro-DL-tryptophan.

A microorganism having tryptophan analogue resistance can be obtained by subjecting a microorganism having an indolmycin-producing ability to a mutation-inducing treatment ordinarily employed in manipulating microorganisms followed by screening for a strain capable of growing in a tryptophan analogue-containing medium described above. Such mutation-inducing treatment may for example be (1) a UV irradiation [spores of a microorganism having an indolmycin-producing ability as a parent strain are suspended for example in a 100 mM phosphate buffer (pH7.0) and irradiated for 90 seconds under a 15 W UV lamp placed at a distance of 30 cm] and (2) a chemical treatment for example with N-methyl-N'-nitro-N-nitrosoguanidine (hereinafter sometimes referred to as NTG) [NTG treatment: spores of a microorganism having an indolmycin-producing ability as a parent strain are suspended for example in a 50 mM Tris.HCl buffer (pH8.0) supplemented with 1 mg/ml of NTG and allowed to stand at 30° C. for 1 hour].

Instead of a mutation-inducing treatment, a spontaneous mutation may also be employed to allow a strain to acquire ability of growing in a tryptophan analogue-containing medium, and such strain is encompassed in a microorganism having a tryptophan analogue resistance according to the invention.

A microorganism having an indolmycin-producing ability employed in this invention may be any microorganism having an indolmycin-producing ability, such as a microorganism of Streptomyces (for example, Streptomyces griseus), typically, Streptomyces griseus ATCC 12648 and Streptomyces sp. HC-21(IFO 15984, FERM BP-5571). The microbiological characteristics of Streptomyces sp. HC-21 are found in WO97/49703.

A microorganism having an indolmycin-producing ability and a tryptophan analogue resistance can be obtained as a tryptophan analogue-resistant mutant for example by subjecting an indolmycin-producing microorganism such as Streptomyces griseus ATCC 12648 as a parent strain to a mutation-inducing treatment such as a UV irradiation and an NTG treatment followed by incubating the strain in a medium (such as agar plate) containing a tryptophan analogue described above at a concentration at which the parent strain can not grow followed by screening the resultant colonies. The degree of the resistance of a mutant thus obtained against a tryptophan analogue can be determined for example as follows. Thus, an agar plate, for example as shown in Table 1, is supplemented with a certain amount of a tryptophan analogue (such as 5-fluoro-DL-tryptophan) and inoculated with a loopful of spores containing about $1 \times 10^6$ to about $1 \times 10^8$ spores/ml and then incubated under a condition suitable for the growth of the parent strain (for example at 24° C. for 8 days), whereby determining the concentration of tryptophan analog at which the parent strain can grow. "A microorganism having a tryptophan analogue resistance (a tryptophan analogue-resistant strain)" according to the invention is a mutant which became to be able to grow in a medium (such as agar medium) containing a tryptophan analogue at a concentration at which the parent strain can not grow.

A microorganism having a tryptophan analogue resistance according to the invention may be a microorganism which can grow in a medium (such as agar plate) containing a tryptophan analogue described above at a high concentration. Against 5-fluoro-DL-tryptophan, for example, a microorganism capable of growing at a concentration of 0.1 to 10000 μg/ml, preferably 1 to 5000 μg/ml, more preferably 10 to 2000 μg/ml is employed. Against 6-fluoro-DL-tryptophan, a microorganism capable of growing at a concentration of 50 to 1000 μg/ml, preferably 100 to 800 μg/ml is employed.

By cultivating a microorganism having a tryptophan analogue resistance obtained as described above followed by quantifying indolmycin in the culture broth, a strain giving an increased indolmycin accumulation can be selected.

Examples of a microorganism having an indolmycin-producing ability and a tryptophan analogue resistance are those described in the following Examples including *Streptomyces griseus* 5FW-1-226-9 capable of growing in the presence of 5-FT at 10 μg/ml, *Streptomyces griseus* 5FW-2-8-7 capable of growing in the presence of 5-FT at 2 mg/ml and *Streptomyces griseus* 6FW-1-8-5 capable of growing in the presence of 6FT at 0.5 mg/ml.

*Streptomyces griseus* 5FW-1-226-9 described above was deposited at the Institute for Fermentation (IFO) on Mar. 27, 1998 under the deposition No. IFO 16170 and also at the Industrial Science and Technology of the Ministry of International Trade and Industry (NIBH, 1-1-3, Higashi, Tsukuba, Ibaragi, Japan) on Apr. 30, 1998 under the deposition number FERM BP-6336.

*Streptomyces griseus* 5FW-2-8-7 was deposited at the IFO on Mar. 27, 1998 under the deposition No. IFO 16171 and also at the NIBH on Apr. 30, 1998 under the deposition number FERM BP-6337.

*Streptomyces griseus* 6FW-1-8-5 was deposited at the IFO on May 26, 1998 under the deposition No. IFO 16178 and also at the NIBH on Jun. 1, 1998 under the deposition number FERM BP-6381.

*Streptomyces sp.* HC-21 was deposited at the IFO on Jun. 12, 1996 under the deposition No. IFO 15984 and also at the NIBH on Jun. 25, 1996 under the deposition number FERM BP-5571.

A production method of the invention comprises cultivating a microorganism having an indolmycin-producing ability and a tryptophan analogue resistance to allow indolmycin or its salt to be produced and accumulated in a culture broth and then recovering a product.

In this method, a microorganism can be cultured by any ordinary culture method such as cultivation with or without shaking, cultivation with aeration and agitation (for example batch culture or fed-batch culture). For a large scale fermentation, cultivation with aeration and agitation is preferred.

For the purpose of maintaining the dissolved oxygen in a culture at a level suitable to the growth of a microorganism and also to the production of indolmycin by said microorganism, an incubation with aeration and agitation for supplying oxygen as desired may also be employed.

While the medium employed in such incubation may be liquid or solid as long as it contains nutrients which allow the growth of the microorganism employed, a large scale fermentation preferably employs a liquid medium.

Such medium may contain any assimilable carbon sources, digestive nitrogen sources, inorganic salts, trace nutrients and the like as desired. A carbon source may for example be glucose, lactose, sucrose, maltose, dextrin, starch, mannitol, sorbitol, glycerol, fats (e.g., soybean oil, olive oil, rice bran oil, sesame oil, lard, chicken oil), various fatty acids (e.g., lauric acid, myristic acid, palmitic acid, stearic acid, oleic acid) and the like. A nitrogen source may for example be meat extract, yeast extract, dried yeast, soybean flour, soybean meal, corn steep liquor, polypeptone, peptone, cottonseed meal, molasses, urea, thiourea, ammonia, ammonium salts (e.g., ammonium sulfate, ammonium chloride, ammonium nitrate, ammonium acetate) and the like. An inorganic salt may for example be sulfate, hydrochloride, carbonate, nitrate, phosphate, acetate and borate of sodium, potassium, copper, calcium, magnesium, iron, manganese, zinc, cobalt, nickel and the like. A trace nutrient may for example be amino acids (e.g., glutamic acid, aspartic acid, alanine, lysine, valine, methionine, proline), peptides (e.g., dipeptide, tripeptide), vitamins (e.g., Vitamin $B_1$, Vitamin $B_2$, nicotinic acid, Vitamin $B_{12}$, Vitamin C and derivatives thereof), nucleic acids (e.g., purine nucleotide, pyrimidine nucleotide and derivatives thereof), which may be added for the purpose of promoting the microbial growth or increasing the product yield.

Otherwise, for the purpose of adjusting the pH of the medium, an inorganic or organic acid or alkali may also be added, or an antifoam agent such as a surfactant (for example Silicon KM70 ("SHINETSU KAGAKU") or "ACTCOL" 31–56 ("TAKEDA CHEMICAL INDUSTRIES") may be added in an amount by which the microbial growth is not adversely affected.

The pH of the medium is about 4 to 9, preferably about 5 to 8. While the medium may previously be supplemented with a phosphate buffer or potassium carbonate in order to keep the pH within the range specified above, it is supplemented with an alkali hydroxide, aqueous ammonia or an ammonia gas when the pH becomes lower than a desired level or with a mineral acid such as hydrochloric acid or sulfuric acid or an organic acid such as acetic acid or citric acid when the pH becomes higher than a desired level.

When a microorganism having an indolmycin-producing ability and a tryptophan analogue resistance according to the invention is cultivated, L-tryptophan is added to a medium at 0.01 to 1% (0.1 to 10 g per 1 L), preferably at 0.02 to 0.5% (0.2 to 5 g per 1 L), more preferably at 0.02 to 0.3% (0.2 to 3 g per 1 L) for the purpose of increasing the indolmycin production. For the same purpose, anthranilic acid may also be added. In such case, anthranilic acid is added to a medium at 0.01 to 6% (0.1 to 60 g per 1 L), preferably at 0.02 to 1% (0.2 to 10 g per 1 L), more preferably at 0.02 to 0.2% (0.2 to 2 g per 1 L).

As a matter of course, each of L-tryptophan and anthranilic acid may be added alone or in combination with each other to the medium.

While anthranilic acid is less expensive when compared with L-tryptophan, it may sometimes be inhibitory on the growth of a producing microorganism. Accordingly, it may give a successful result when combined with L-tryptophan. In such case, the concentration of each component may be adjusted to achieve an acceptable expenditure, less growth inhibition and maximum indolmycin production. When both of L-tryptophan and anthranilic acid are added, each may be added in an amount smaller than that when added alone, and 1 L of a medium may be supplemented with L-tryptophan at 0.01 to 0.5% (0.1 to 5 g), preferably 0.02 to 0.3% (0.2 to 3 g) and with anthranilic acid at 0.02 to 1% (0.2 to 10 g), preferably 0.02 to 0.2% (0.2 to 2 g).

L-Tryptophan may be added to the medium at once at the initiation of cultivation or intermittently during cultivation. Anthranilic acid is added intermittently at the initiation of and/or during cultivation so that microbial growth is not adversely affected, whereby obtaining a successful result.

The culture temperature is a temperature which is suitable for the growth of a microorganism employed and also for the extracellular accumulation of indolmycin (for example, about 10 to 40° C., such as about 22 to 30° C. for *Streptomyces griseus* and a mutant thereof and about 18 to 28° C. for *Streptomyces sp.* HC-21 and a mutant thereof).

While the culture time may be appropriately selected based on the culture condition, the cultivation may be continued until the accumulated indolmycin per unit volume of culture broth reaches maximal production, for example, over a period usually of about 2 days to 2 weeks.

In a method of the invention, indolmycin is contained mainly in the culture supernatant. Accordingly, the culture broth after completing the cultivation is subjected to a separation method known per se (e.g., centrifugation, filter pressing, ultrafiltration, ceramic filtration and other forcible filtration) to remove the cells, and the resultant filtrate is subjected to a separation and purification to yield indolmycin. In such procedure, an aggregation agent may previously be added or a heat treatment may be employed as desired. In order to recover indolmycin as being purified from a filtrate or supernatant obtained as described above, a known purification method ordinarily employed for purifying an fat-soluble substance, such as extraction with an organic solvent immiscible with water (for example ethyl acetate, isobutanol, methylisobutylketone and the like) followed by concentration, may be employed.

In the invention, a method described below, wherein a purification is performed using an adsorption resin, a basic anion exchange resin and/or an acidic cation exchange resin as a support and an aqueous organic solvent as an eluent, is employed to achieve a high yield production of indolmycin at a low cost.

Thus, a resultant filtrate is first loaded on an adsorption resin [e.g., "DIAION" HP-20, "SEPABEADS" SP-207 or SP-850 ("MITSUBISHI KAGAKU"), XAD-2 (Rohm & Haas, USA), preferably "SEPABEADS" SP-850] at pH 5 to 9 to allow indolmycin to be adsorbed. The resin is then washed with an alkaline solution at a concentration of 0.01 to 1 M (e.g., sodium hydroxide, potassium hydroxide, sodium carbonate, ammonia and the like) and an acid at a concentration of 0.01 to 1 M (e.g., hydrochloric acid, sulfuric acid, phosphoric acid). In this procedure, the order of the alkaline and acid washing steps may be inverted, and the steps may be repetitively performed. Subsequently, the resin is washed further with 5 to 30% aqueous alcohol (e.g., methanol, ethanol, isopropyl alcohol) and indolmycin is then eluted with 20 to 60% aqueous alcohol. By completing the washing and elution steps with the aqueous alcohols at a temperature of about 30 to 50° C., the volume of an eluent can be reduced.

The eluent thus obtained is then loaded on a basic anion exchange resin and/or an acidic cation exchange resin as a support to continue the purification.

Such basic anion exchange resin may for example be "DIAION" PA-412, PA-306, SA21A or WA-30 ("MITSUBISHI KAGAKU"), Amberlite IRA-402 (Rohm & Haas, USA), Dowex 1 (Dow Chemical, USA), as well as a weakly basic anion exchange resin such as Amberlite IRA-67 (Rohm & Haas, USA), with a weakly basic anion exchange resin being particularly preferred.

A cation exchange resin described above may for example be Amberlite IR-120B, IR-200C (Rohm & Haas, USA), Dowex 50 W (Dow Chemical, USA), "DIAION" PK-216 ("MITSUBISHI KAGAKU"), as well as a weakly—acidic cation exchange resin such as Amberlite IRC-50 (Rohm & Haas, USA), "LEWATIT" CNP-80 (Bayer, Germany), with a weakly-acidic cation exchange resin being particularly preferred.

In addition to the loading on a resin described above, an activated charcoal treatment (e.g., activated charcoal for chromatography (TAKEDA CHEMICAL INDUSTRIES) may be employed alone, in combination or sequentially, and the resin is washed preferably with an aqueous alcohol described above.

The resultant effluent and washings are combined and concentrated under reduced pressure to yield indolmycin as a crystal. The mixture to be concentrated under reduced pressure may be combined with an alcohol (e.g. methanol, ethanol, isopropyl alcohol) in an amount of about 20 to 50% based on the mixture to be concentrated under reduced pressure, whereby increasing the resultant crystal content. Recrystallization from aqueous alcohol (30 to 60% methanol or ethanol) may be performed, if necessary, to yield a further highly purified crystal.

Indolmycin obtained in this invention is useful as a pharmaceutical (for example, an antibacterial agent, especially anti-H.pylori agent), a veterinary agent and a herbicide.

BEST MODE FOR CARRYING OUT THE INVENTION

The present invention is further detailed in the following Examples, which are not intended to restrict the invention. "%" shown in the medium means weight/weight %.

EXAMPLES

Example 1

*Streptomyces griseus* ATCC 12648 was irradiated with a UV light (for 90 seconds under a 15 W UV lamp placed at a distance of 30 cm) to obtain an indolmycin-hyperproducing mutant *Streptomyces griseus* RS-1-67-7. Strain RS-1-67-7 was subjected according to an ordinary method to an N-methyl-N'-nitro-N-nitrosoguanidine treatment (hereinafter referred to as an NTG treatment; spores were suspended in a 50 mM Tris.HCl buffer (pH 8.0) containing 1 mg/ml of NTG and allowed to stand for 1 hour) and then spread on an agar plate medium shown in Table 1 containing 10 μg/ml of 5-fluoro-DL-tryptophan, where the strain was incubated at 24° C. for 7 days. The colonies grown on this agar plate were screened for an indolmycin-hyperproducing mutant to obtain *Streptomyces griseus* 5FW-1-226-9. A 200 ml conical flask containing 20 ml of the seed medium having the composition shown in Table 3 was inoculated with a loopfull of the strain 5FW-1-226-9 grown on an agar slant having the composition shown in Table 2 and incubated at 24° C. for 48 hours with shaking, and a 0.5 ml aliquot was inoculated to a 200 ml conical flask containing 20 ml of the main medium having the composition shown in Table 4, which was cultivated on a rotary shaker at 24° C. for 6 days. High performance liquid chromatography (HPLC) to determine the level of indolmycin accumulated in the culture broth of the strain 5FW-1-226-9 described above after completing the cultivation revealed the production of 240 μg/ml.

The parent strain RS-1-67-7 was similarly cultivated and gave the production of 130 μg/ml. Thus, an acquired 5-FT resistance resulted in a production increase of 1.8 times.

Example 2

The main medium supplemented with 0.05% L-tryptophan shown in Table 4 was employed to cultivate the strain 5FW-1-226-9 under the conditions in Example 1.

The indolmycin production in the culture broth after completing the cultivation was 240 μg/ml in the absence of L-tryptophan (Example 1) which was in contrast with the production of 320 μg/ml in the presence of L-tryptophan at 0.05%. Thus, the addition of L-tryptophan at 0.05% resulted in a production increase of 1.5 times.

On the other hand, the parent strain RS-1-67-7 incubated under the same conditions gave indolmycin production of 130 μg/ml in the absence of L-tryptophan and 70 μg/ml in the presence of L-tryptophan.

Example 3

Streptomyces griseus 5FW-1-226-9 was subjected to an NTG treatment similarly to Example 1 to obtain Streptomyces griseus 5FR-2-8-7 as an indolmycin-hyperproducing mutant capable of growing on an agar plate which had the composition shown in Table 1 and was supplemented with 2 mg/ml of 5-fluoro-DL-tryptophan. A loopful of strain 5FR-2-8-7 grown on a slant medium having the composition shown in Table 2 was inoculated to a 200 ml conical flask containing 20 ml of a seed medium having the composition shown in Table 5, which was cultivated at 24° C. for 48 hours and a 0.5 ml aliquot of the culture was inoculated to a 200 ml conical flask containing 20 ml of the main medium having the composition shown in Table 6, which was incubated on a rotary shaker at 24° C. for 8 days. A HPLC to determine the level of indolmycin accumulated in the culture broth after completing the cultivation revealed the production of 557 μg/ml. The parent strain 5FW-1-226-9 was cultivated under the same condition and gave the indolmycin production of 325 μg/ml.

When strain 5FW-2-8-7 was cultivated under the condition described above in the main medium which had the composition shown in Table 6 and was supplemented with 0.05% L-tryptophan, the production of indolmycin accumulated in the culture broth was 1029 μg/ml.

Example 4

Streptomyces griseus 5FW-2-8-7 was subjected to an NTG treatment similarly to Example 1 and then spread on an agar plate which was supplemented with 500 μg/ml of 6-fluoro-DL-tryptophan and had the composition shown in Table 1, which was incubated at 24° C. for 7 days. The colonies grown on this agar plate were screened for an indolmycin-hyperproducing mutant to obtain Streptomyces griseus 6FW-1-8-5. A 200 ml conical flask containing 20 ml of the seed medium having the composition shown in Table 7 was inoculated with a loopful of the strain 6FW-1-8-5 grown on an agar slant having the composition shown in Table 2 and incubated at 24° C. for 48 hours with shaking, and a 0.5 ml aliquot was inoculated to a 200 ml conical flask containing 20 ml of the main medium having the composition shown in Table 8, which was incubated on a rotary shaker at 24° C. for 11 days. A HPLC to determine the level of indolmycin accumulated in the culture broth after completing the cultivation revealed the production of 1335 μg/ml.

The parent strain 5FW-2-8-7 was incubated under the same condition and gave the indolmycin production of 827 μg/ml.

Example 5

1 ml of a frozen stock cells of Streptomyces griseus 5FW-2-8-7 was inoculated to a 2.0 L Sakaguchi flask containing 500 ml of a preculture medium having the composition shown in Table 9 and incubated at 28° C. for 48 hours. A 500 ml aliquot was incubated in a 200 L fermenter containing 120 L of the seed medium having the composition shown in Table 10 at 24° C. with the aeration of 120 L/min under the internal pressure of 1 kg/cm$^2$ with agitation at 150 rpm for 48 hours, and the entire culture was transferred to a 6 m$^3$ fermenter containing 4 m$^3$ of the main medium having the composition shown in Table 11, which was then incubated at 24° C. 24 Hours after initiating the incubation, L-tryptophan was added at 0.05%, and then the incubation was further continued with the aeration of 3200 L/min under the internal pressure of 1 kg/cm$^2$ with agitation at a rate varying from 80 to 115 rpm for the purpose of maintaining the lower limit of the dissolved oxygen at 5 ppm or higher, and finally 840 μg/ml of indolmycin was accumulated in the culture broth after the cultivation over 162 hours.

Example 6

The final culture broth (3800 L) obtained in Example 5 was combined with 1500 L of tap water and heated to 60° C. and adjusted at pH 5.0 with sulfuric acid, and then 150 kg of "TOPCO Perlite" No.31 (TOKO PERLITE KOGYO) and 800 L of a 0.2% "SANFLOC" C-109P (SANYO KASEI) were added and filtered through an "OLIVER" filter machine which had previously been coated with 80 kg and 20 kg of "RADIOLITE" 600 and 500S (SHOWA KAGAKU KOGYO), respectively, to obtain a filtrate. This filtrate was adjusted at pH 8.0 with NaOH and loaded on 75 L of "SEPABEADS" SP-850 ("MITSUBISHI KAGAKU"), which was then washed sequentially with 350 L of water, 225 L of a 0.1 mol/L aqueous solution of sodium hydroxide, 225 L of water, 75 L of 0.1 mol/L sulfuric acid, 300 L of water and 225 L of a 20% aqueous solution of isopropyl alcohol, and then eluted with 300 L of 50% aqueous isopropyl alcohol to obtain 243 L of a fraction containing indolmycin. 50% Aqueous isopropyl alcohol-presubstituted IRA-67 (OH type) in the volume of 35 L, CNP-80 (H type) in the volume of 10 L and activated charcoal (PAL-P) in the volume of 4 L were connected reciprocally, and loaded with the fraction containing indolmycin, washed with 50% aqueous isopropyl alcohol to obtain 392 L of the effluent combined with the washing. The mixture was adjusted at pH 5.0 with NaOH, concentrated to 42 L, combined with 14 L of methanol, adjusted at pH6.0 with NaOH and then crystallized to yield 2.6 kg of a crude crystal. The crystal was dissolved in 13 L of methanol and combined with 13 L of water to perform a recrystallization, whereby obtaining 2.3 kg of a purified crystal containing 99% or higher indolmycin.

Example 7

1 ml of a frozen stock cells of *Streptomyces griseus* 6FW-1-8-5 was inoculated to a 2.0 L Sakaguchi flask containing 500 ml of a preculture medium having the composition shown in Table 9 and incubated at 28° C. for 48 hours. A 500 ml aliquot was incubated in a 200 L fermenter containing 120 L of the seed medium having the composition shown in Table 10 at 24° C. with the aeration of 120 L/min under the internal pressure of 1 kg/cm$^2$ with agitation at 150 rpm for 48 hours, and a 100 ml aliquot was transferred to a 5 L jar fermenter containing 3 L of the main medium having the composition shown in Table 12, which was then incubated at 24° C. until 66 hrs after initiation of cultivation, after which the temperature was 28° C.

To this culture broth, anthranilic acid (adjusted at pH 7.0 with NaOH) was added intermittently over a period from Time 0 hr to Time 90 hrs up to the final concentration of 0.05%, and a 234-hour incubation gave the indolmycin production of 1661 μg/ml in the culture broth. On the other hand, the culture supplemented only with a sterilized water gave indolmycin production of 1323 μg/ml.

Example 8

1 ml of frozen stock cells of *Streptomyces griseus* 6FW-1-8-5 was inoculated to a 2.0 L Sakaguchi flask containing 500 ml of a preculture medium having the composition shown in Table 9 and incubated at 28° C. for 48 hours. A 500 ml aliquot was incubated in a 200 L fermenter containing 120 L of the seed medium having the composition shown in Table 10 at 24° C. with an aeration of 120 L/min under internal pressure of 1 kg/cm$^2$ with agitation at 150 rpm for 48 hours, and a 100 ml aliquot was transferred to a 5 L jar fermenter containing 3 L of the main medium having the composition shown in Table 12, which was then cultivated at 24° C. until Time 66 hrs, after which the temperature was 28° C.

L-Tryptophan and anthranilic acid (adjusted at pH 7.0 with NaOH) were added intermittently over a period from Time 0 hr to Time 90 hrs up to the each final concentration of 0.1%, and a 234-hour incubation gave the indolmycin production of 1831 μg/ml in the culture broth. On the other hand, the culture supplemented only with sterilized water gave an indolmycin production of 1323 μg/ml.

The composition of each medium employed in each Example described above is shown below.

TABLE 1

| Medium composition | Concentration (%) |
| --- | --- |
| Glucose | 1.0 |
| L-Asparagine | 0.05 |
| K$_2$HPO$_4$ | 0.05 |
| MgSO$_4$.7H$_2$O | 0.02 |
| FeSO$_4$.7H$_2$O | 0.001 |
| (pH 7.0) | |
| Agar | 2.0 |

TABLE 2

| Medium composition | Concentration (%) |
| --- | --- |
| Maltose | 0.8 |
| Yeast extract | 0.08 |
| Meat extract | 0.08 |
| Bactotryptone | 0.1 |
| (pH 7.0) | |
| Agar | 2.0 |

TABLE 3

| Medium composition | Concentration (%) |
| --- | --- |
| Purified glucose | 2.0 |
| Soluble starch | 3.0 |
| Soybean flour | 1.0 |
| Corn steep liquor | 0.3 |
| Yeast extract | 0.3 |
| Polypeptone | 0.1 |
| NaCl | 0.3 |
| (pH 7.0) | |
| CaCO$_3$ | 0.5 |

TABLE 4

| Medium composition | Concentration (%) |
| --- | --- |
| Purified glucose | 4.0 |
| Soybean meal | 3.0 |
| Corn steep liquor | 0.6 |
| Yeast extract | 0.2 |
| NaCl | 0.06 |
| FeSO$_4$.7H$_2$O | 0.05 |
| ZnSO$_4$.7H$_2$O | 0.02 |
| (pH 7.0) | |
| CaCO$_3$ | 0.1 |

TABLE 5

| Medium composition | Concentration (%) |
| --- | --- |
| Purified glucose | 0.5 |
| Soluble starch | 3.0 |
| Soybean flour | 1.0 |
| Corn steep liquor | 0.3 |
| Yeast extract | 0.5 |
| Polypeptone | 0.1 |
| NaCl | 0.3 |
| (pH 7.0) | |
| CaCO$_3$ | 0.5 |

TABLE 6

| Medium composition | Concentration (%) |
| --- | --- |
| Purified glucose | 6.0 |
| Defatted soybean flake | 3.0 |
| Corn steep liquor | 0.6 |
| Yeast extract | 0.2 |
| NaCl | 0.06 |
| FeSO$_4$.7H$_2$O | 0.05 |
| ZnSO$_4$.7H$_2$O | 0.02 |
| β-Cyclodextrin | 1.0 |
| (pH 7.0) | |
| CaCO$_3$ | 0.1 |

TABLE 7

| Medium composition | Concentration (%) |
|---|---|
| Purified glucose | 2.0 |
| Soluble starch | 3.0 |
| Soybean meal | 2.0 |
| Corn steep liquor | 0.3 |
| Yeast extract | 0.5 |
| Polypeptone | 0.1 |
| NaCl | 0.3 |
| (pH 7.0) | |
| $CaCO_3$ | 0.5 |

TABLE 8

| Medium composition | Concentration (%) |
|---|---|
| Purified glucose | 10.0 |
| Soybean meal | 4.0 |
| Corn steep liquor | 1.0 |
| Yeast extract | 0.2 |
| $FeSO_4.7H_2O$ | 0.05 |
| $ZnSO_4.7H_2O$ | 0.02 |
| (pH 7.0) | |
| $CaCO_3$ | 0.3 |
| ACTCOL | 0.01 |

TABLE 9

| Medium composition | Concentration (%) |
|---|---|
| Purified glucose | 2.0 |
| Soluble starch | 3.0 |
| Defatted soybean flake | 2.0 |
| (pH 7.0) | |
| $CaCO_3$ | 0.5 |

TABLE 10

| Medium composition | Concentration (%) |
|---|---|
| Purified glucose | 2.0 |
| Soluble starch | 3.0 |
| Soybean meal | 2.0 |
| (pH 7.0) | |
| $CaCO_3$ | 0.5 |
| ACTCOL | 0.05 |
| Silicon oil | 0.05 |

TABLE 11

| Medium composition | Concentration (%) |
|---|---|
| Purified glucose | 7.0 |
| Soybean meal | 4.0 |
| Corn steep liquor | 1.0 |
| Yeast extract | 0.2 |

TABLE 11-continued

| Medium composition | Concentration (%) |
|---|---|
| NaCl | 0.06 |
| $FeSO_4.7H_2O$ | 0.05 |
| $ZnSO_4.7H_2O$ | 0.02 |
| (pH 7.0) | |
| $CaCO_3$ | 0.3 |
| ACTCOL | 0.05 |
| Silicon oil | 0.05 |

TABLE 12

| Medium composition | Concentration (%) |
|---|---|
| Purified glucose | 10.0 |
| Soybean meal | 5.0 |
| Corn steep liquor | 0.3 |
| Yeast extract | 0.5 |
| $FeSO_4.7H_2O$ | 0.05 |
| $ZnSO_4.7H_2O$ | 0.05 |
| ACTCOL | 0.05 |
| Silicon | 0.05 |
| (pH 7.0) | |
| $CaCO_3$ | 0.3 |

Industrial Applicability

The present invention enables an efficient production of indolmycin. Thus, by using a mutant having resistance to a tryptophan analogue and cultivating the mutant in a medium, a large amount of indolmycin can be obtained from the culture broth. In addition, by supplementing the medium with tryptophan and performing a cultivation, the amount of accumulated indolmycin per unit volume of culture broth can greatly be increased. Accordingly, a large scale industrial production of indolmycin is possible.

What is claimed is:

1. An isolated microorganism of *Streptomyces griseus* having all the identifying characteristics of *Streptomyces griseus* strain 5FW-1-226-9, deposited with the NIBH, having an accession number of FERM BP-6336.

2. An isolated microorganism of *Streptomyces griseus* having all the identifying characteristics of *Streptomyces griseus* strain 5FW-2-8-7, deposited with the NIBH, having an accession number of FERM BP-6337.

3. An isolated microorganism of *Streptomyces griseus* having all the identifying characteristics of *Streptomyces griseus* strain 6FW-1-8-5, deposited with the NIBH, having an accession number of FERM BP-6381.

4. A method for producing indolmycin or its salt comprising cultivating a microorganism of *Streptomyces griseus* strain 5FW-1-226-9; *Streptomyces griseus* strain 5FW-2-8-7; or *Streptomyces griseus* strain 6FW-1-8-5 in a medium to allow indolmycin or its salt to be accumulated in the culture broth; and then, recovering indolmycin.

* * * * *